(12) United States Patent
Moon

(10) Patent No.: US 10,792,133 B2
(45) Date of Patent: Oct. 6, 2020

(54) 3D SCANNER AND ARTIFICIAL OBJECT PROCESSING DEVICE USING THE SAME

(71) Applicant: DDS Company, Seoul (KR)

(72) Inventor: Jung Bon Moon, Busan (KR)

(73) Assignee: DDS COMPANY, Seoul (KR)

(*) Notice: Subject to any disclaimer, the term of this patent is extended or adjusted under 35 U.S.C. 154(b) by 11 days.

(21) Appl. No.: 16/316,063

(22) PCT Filed: Jul. 12, 2017

(86) PCT No.: PCT/KR2017/007436
§ 371 (c)(1),
(2) Date: Jan. 8, 2019

(87) PCT Pub. No.: WO2018/012862
PCT Pub. Date: Jan. 18, 2018

(65) Prior Publication Data
US 2019/0254783 A1   Aug. 22, 2019

(30) Foreign Application Priority Data

Jul. 13, 2016  (KR) .................. 10-2016-0088926
Jul. 13, 2016  (KR) .................. 10-2016-0088930

(51) Int. Cl.
| | | |
|---|---|---|
| *A61C 9/00* | (2006.01) | |
| *B33Y 30/00* | (2015.01) | |
| *B33Y 50/00* | (2015.01) | |
| *B33Y 80/00* | (2015.01) | |
| *A61B 1/00* | (2006.01) | |
| *A61B 1/24* | (2006.01) | |
| *A61C 13/00* | (2006.01) | |

(Continued)

(52) U.S. Cl.
CPC .......... *A61C 9/006* (2013.01); *A61B 1/00016* (2013.01); *A61B 1/00045* (2013.01); *A61B 1/24* (2013.01); *A61B 5/00* (2013.01); *A61C 9/00* (2013.01); *A61C 13/00* (2013.01); *A61C 13/0019* (2013.01); *A61C 13/01* (2013.01); *A61C 13/08* (2013.01); *A61C 19/04* (2013.01); *B33Y 30/00* (2014.12); *B33Y 50/00* (2014.12); *B33Y 80/00* (2014.12); *G02B 3/04* (2013.01); *G02B 26/0833* (2013.01); *G02B 26/10* (2013.01); *G02B 27/30* (2013.01)

(58) Field of Classification Search
CPC ... A61B 1/00016; A61B 1/00045; A61B 1/24; A61B 5/00; A61C 9/00; A61C 9/006; A61C 13/00; A61C 13/0019; A61C 13/01; A61C 13/08; A61C 19/04
USPC ........................................................ 356/603
See application file for complete search history.

(56) References Cited

U.S. PATENT DOCUMENTS

| 6,977,732 B2* | 12/2005 | Chen ...................... G01B 11/25 356/603 |
| 7,184,150 B2* | 2/2007 | Quadling ............. A61B 5/0088 356/602 |

(Continued)

OTHER PUBLICATIONS

International Search Report of PCT/KR2017/007436, dated Nov. 14, 2017, English translation

*Primary Examiner* — Roy M Punnoose
(74) *Attorney, Agent, or Firm* — STIP Law Group, LLC

(57) ABSTRACT

A 3D scanner according to an embodiment of the present invention includes a pattern generating device irradiating a light pattern to a subject and an imaging device receiving an omni-directional image of the subject to which the light pattern is irradiated.

19 Claims, 14 Drawing Sheets

(51) Int. Cl.
*A61C 13/01* (2006.01)
*A61C 13/08* (2006.01)
*G02B 3/04* (2006.01)
*G02B 26/08* (2006.01)
*G02B 26/10* (2006.01)
*G02B 27/30* (2006.01)
*A61B 5/00* (2006.01)
*A61C 19/04* (2006.01)

(56) References Cited

U.S. PATENT DOCUMENTS

| | | | | |
|---|---|---|---|---|
| 7,573,583 B2 * | 8/2009 | Quadling | ............ | A61C 9/0053 |
| | | | | 356/602 |
| 8,488,113 B2 * | 7/2013 | Thiel | .................... | G01B 11/026 |
| | | | | 356/73 |
| 9,980,651 B2 * | 5/2018 | Pfeiffer | .............. | G01B 11/2441 |
| 2011/0080576 A1 * | 4/2011 | Thiel | .................... | G01B 11/026 |
| | | | | 356/73 |

\* cited by examiner

[Fig. 1]
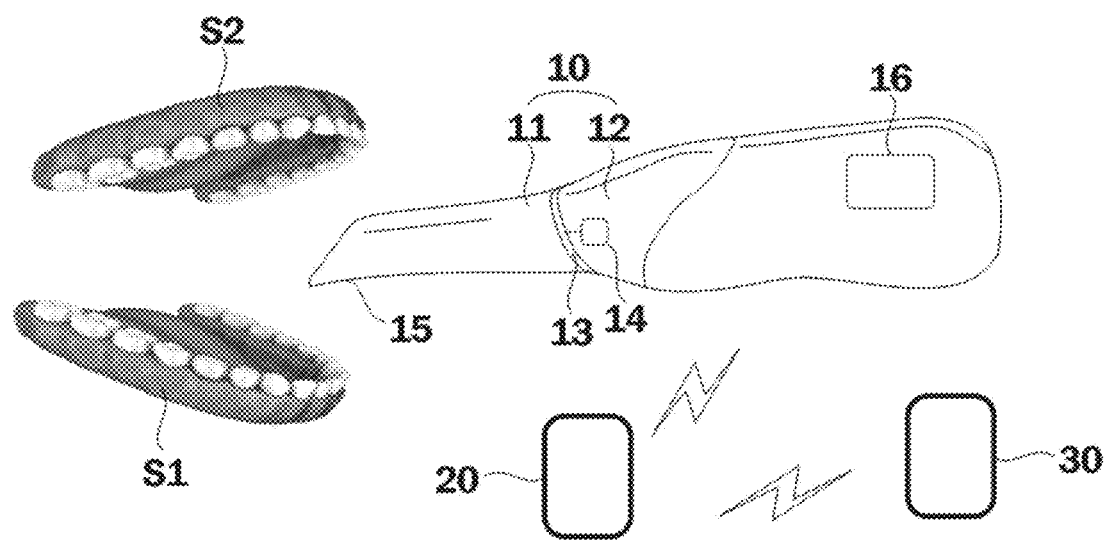
[Fig. 2]
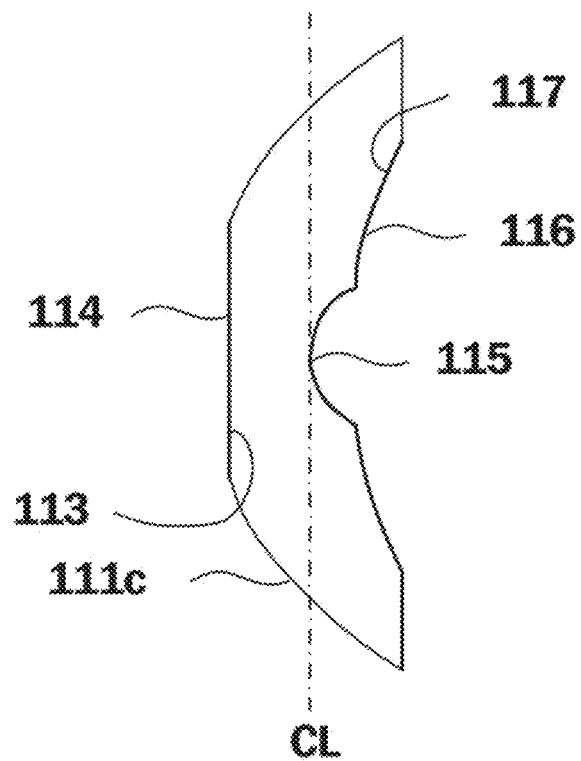

[Fig. 3]
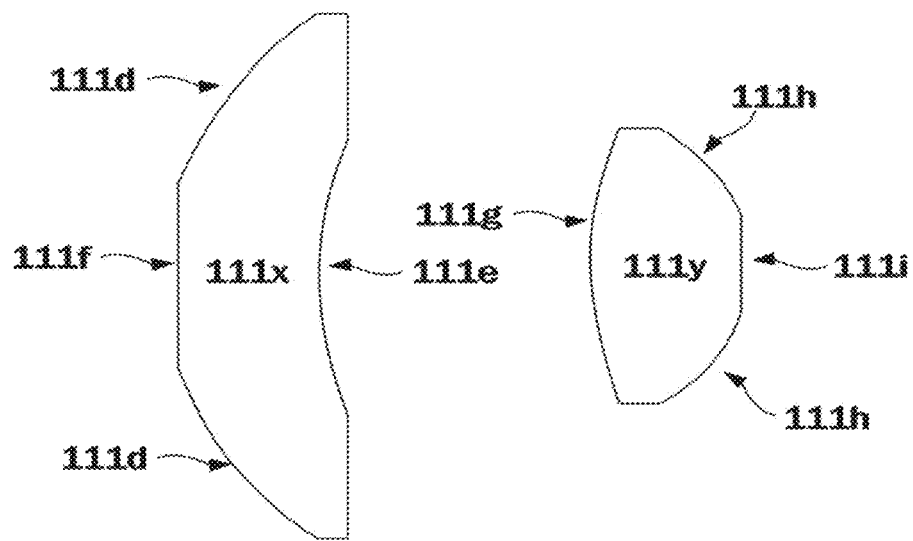
[Fig. 4]
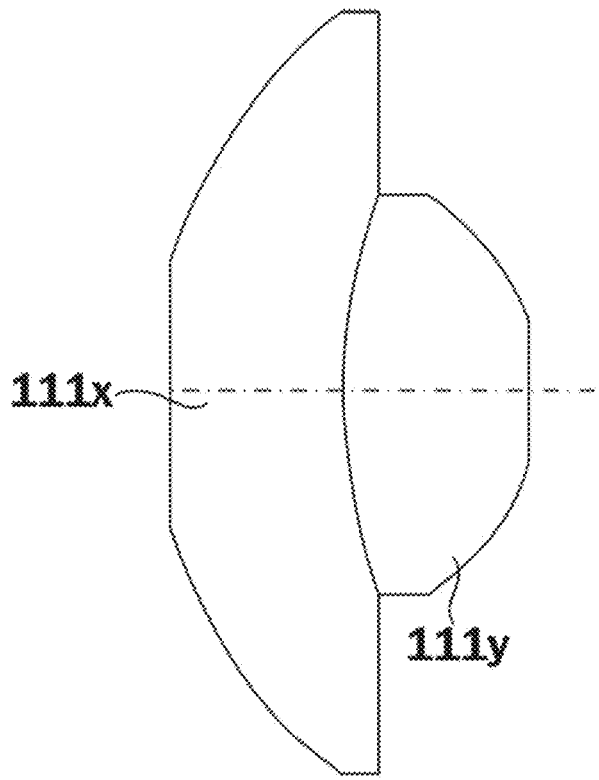

[Fig. 5]
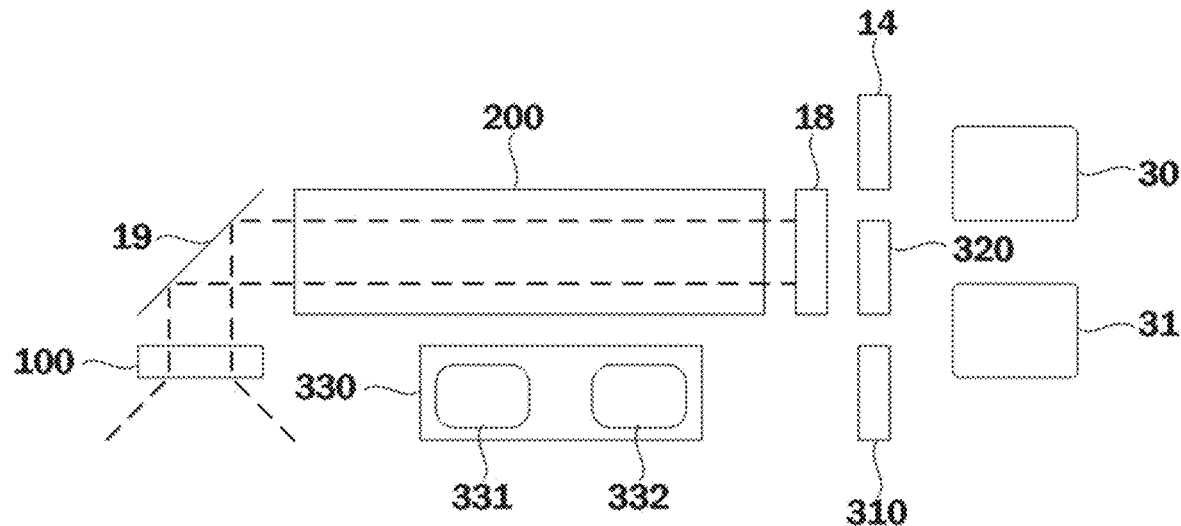
[Fig. 6]
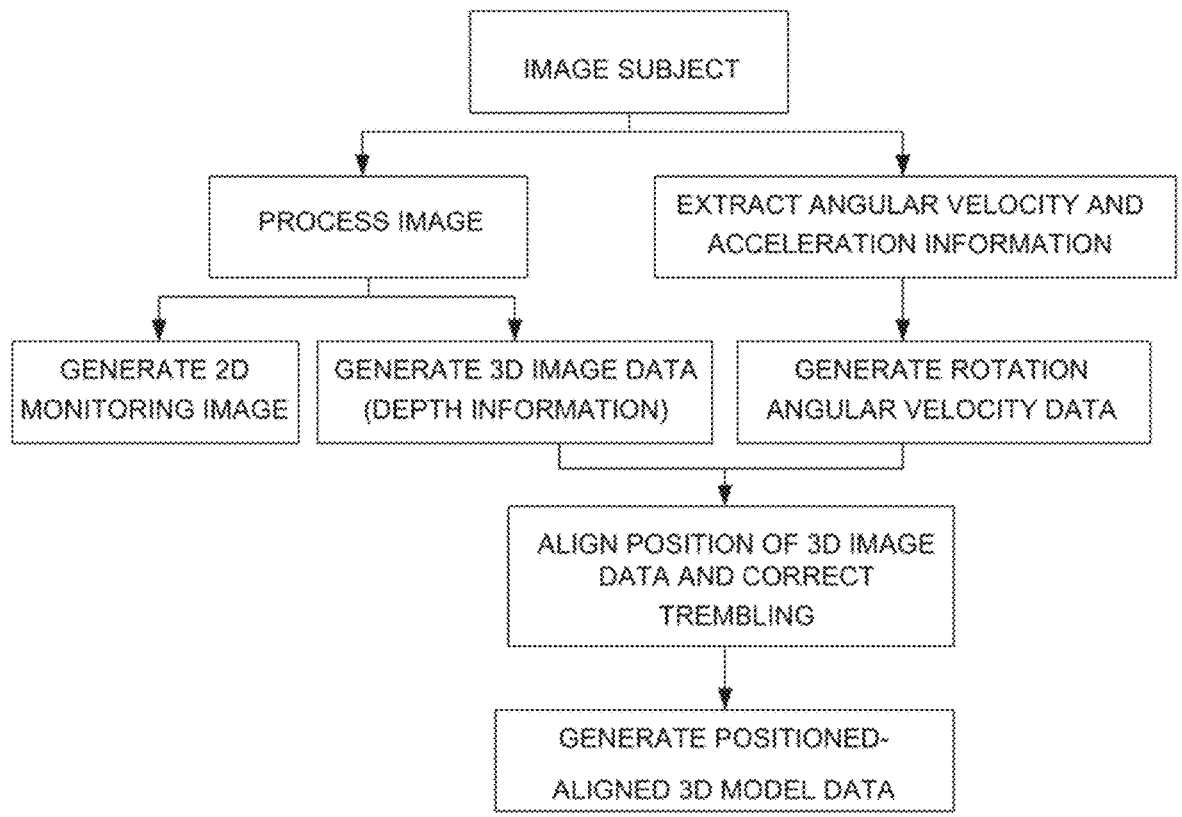

[Fig. 7]
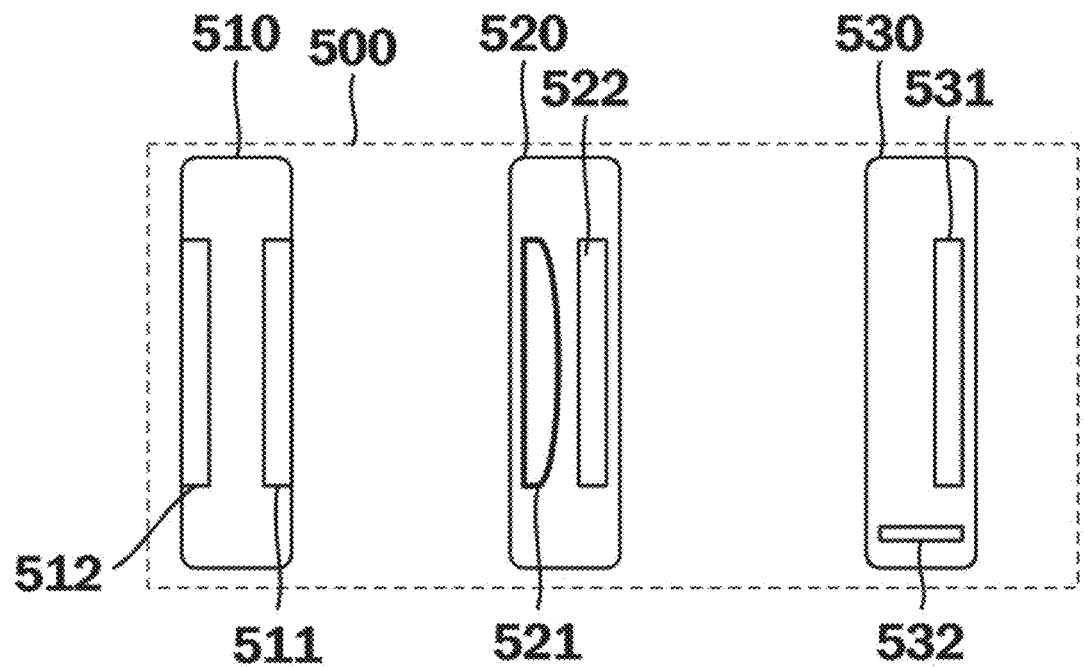
[Fig. 8]
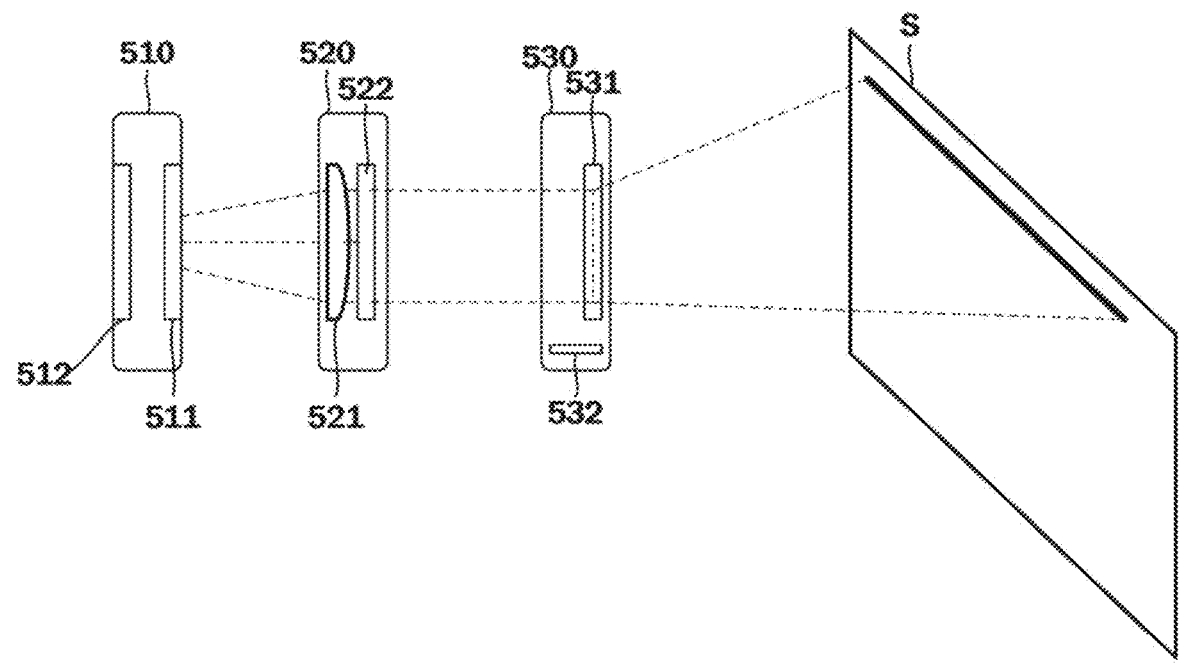

[Fig. 9]
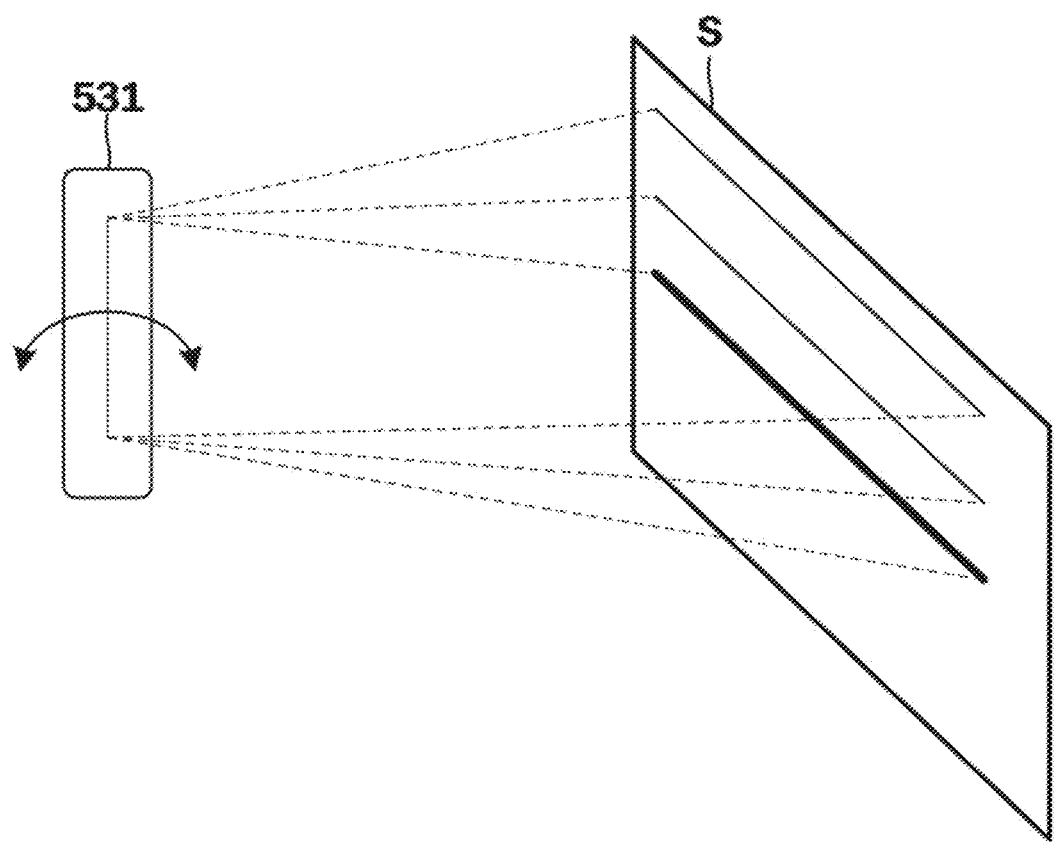

[Fig. 10]
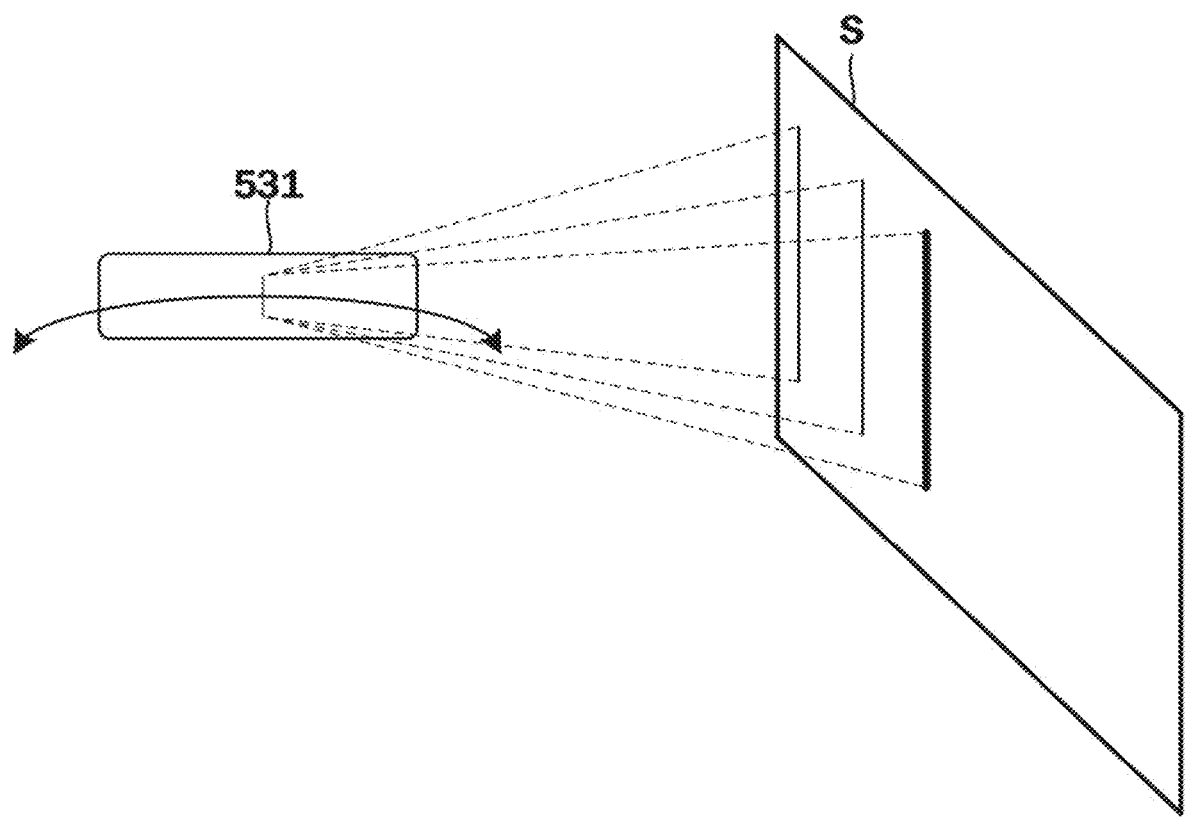

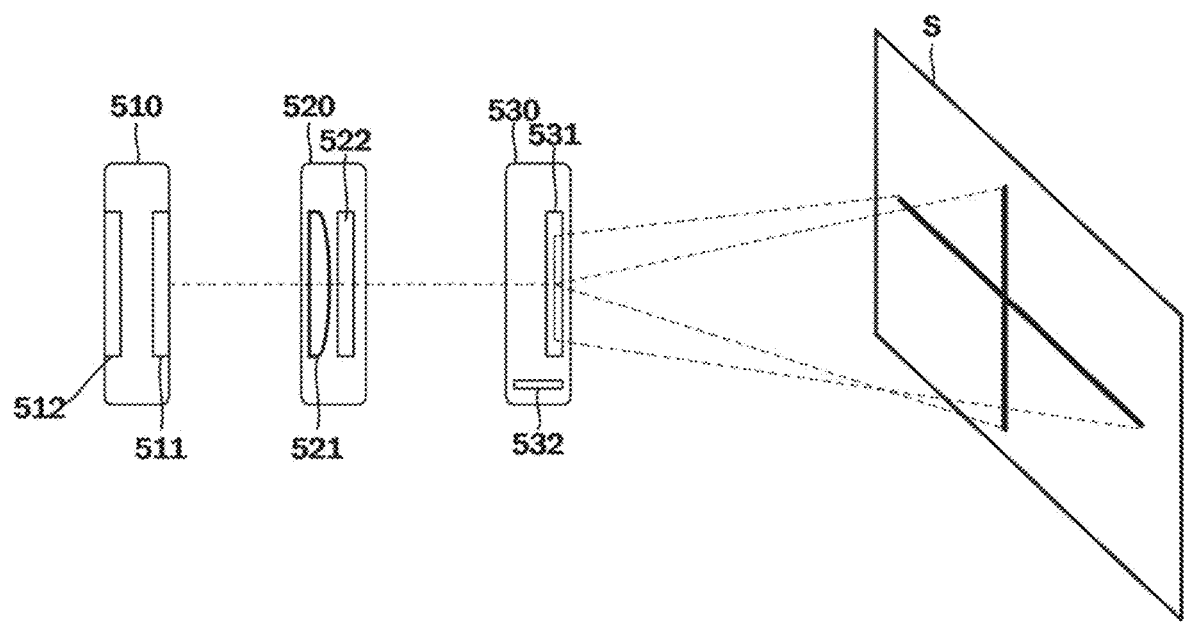
[Fig. 11]

[Fig. 12]
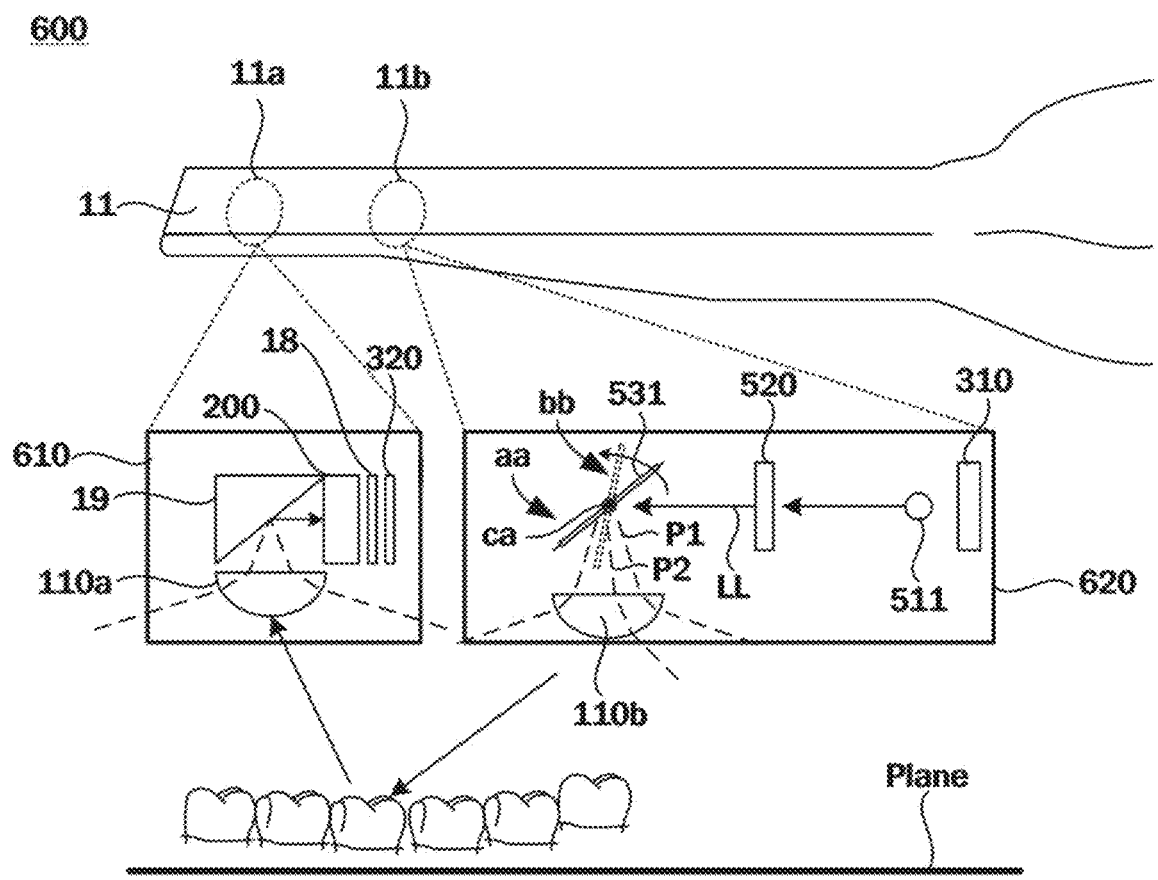

[Fig. 13]
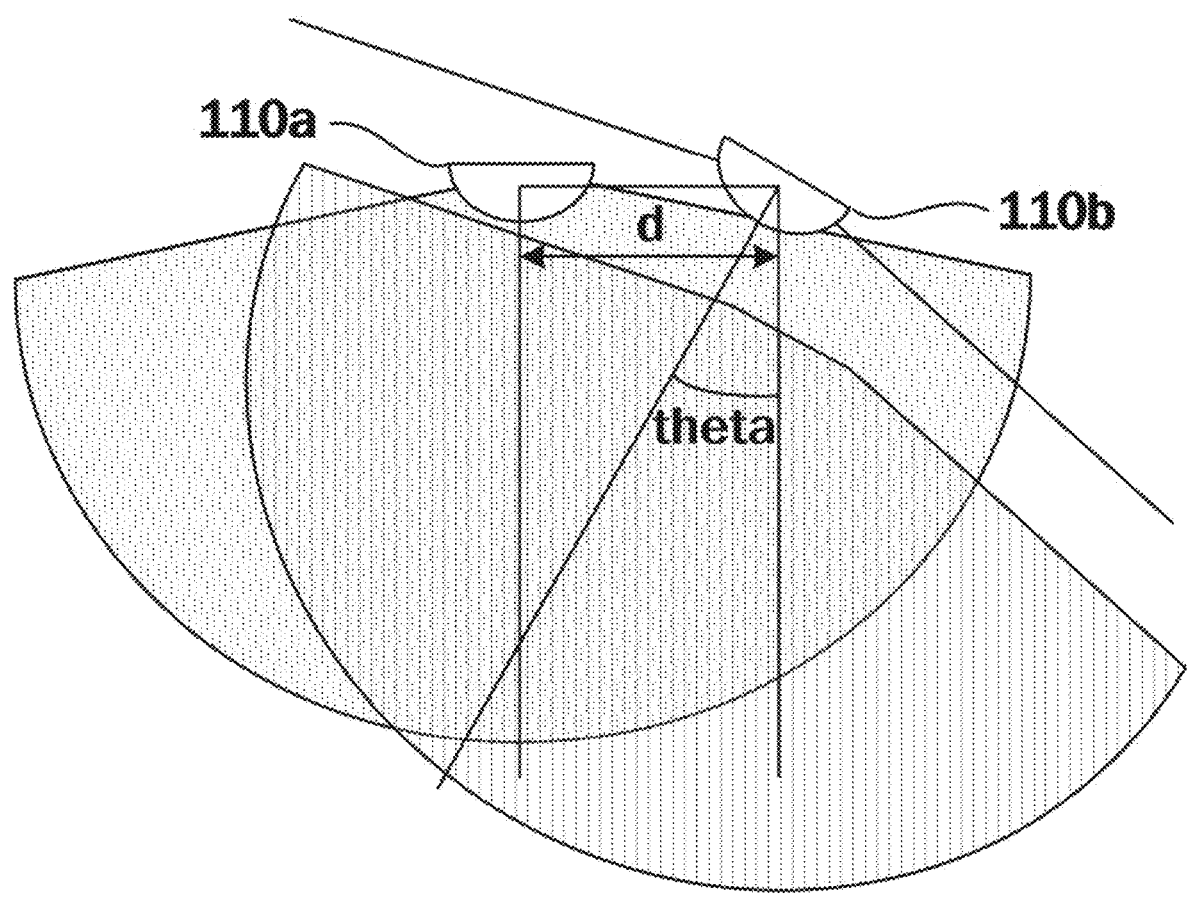

[Fig. 14]
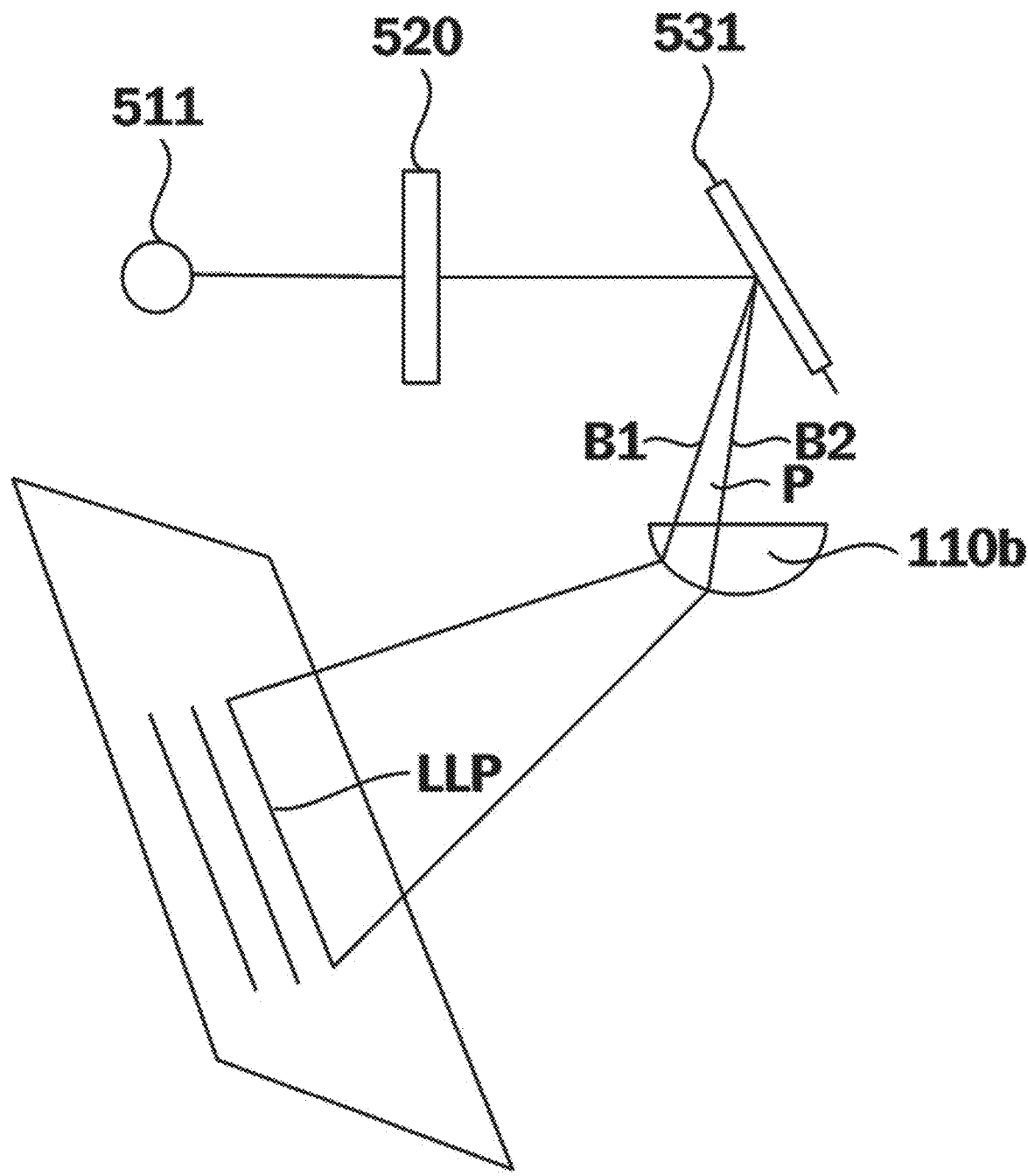

[Fig. 15]
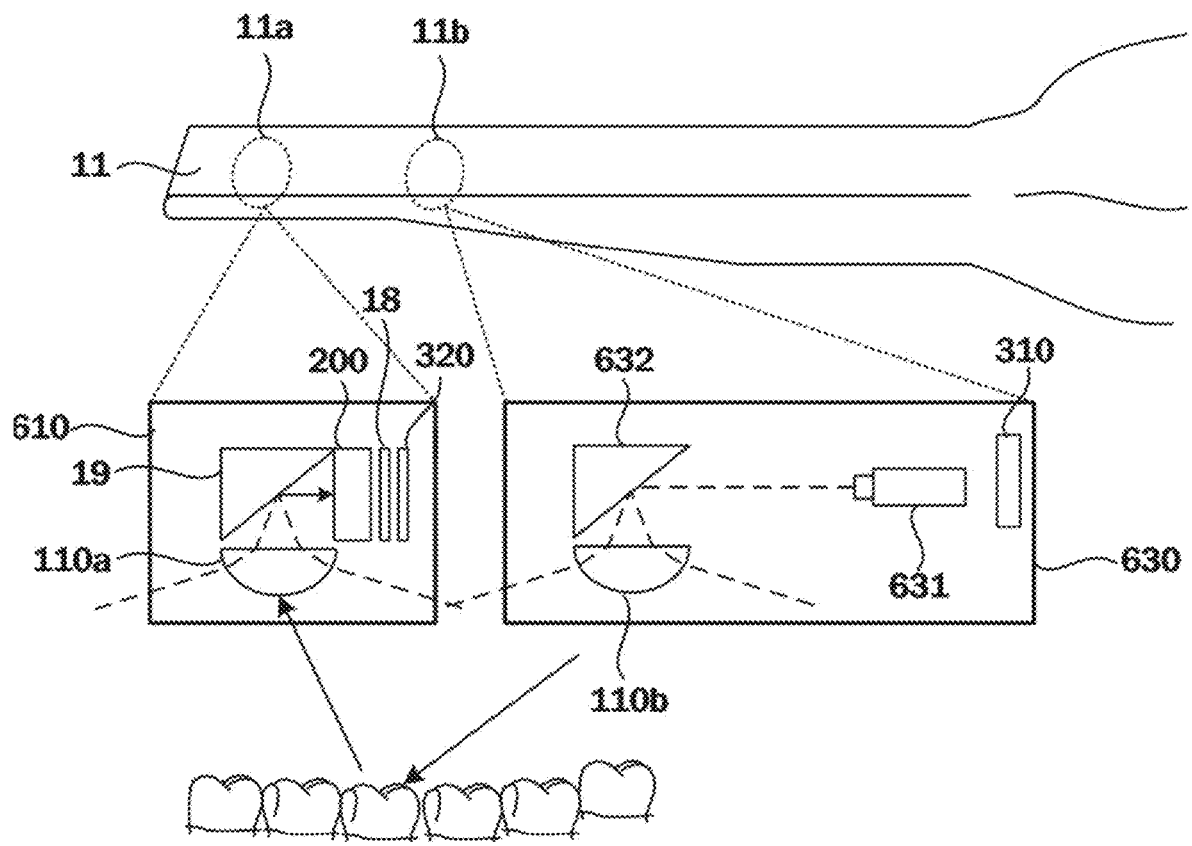

[Fig. 16]
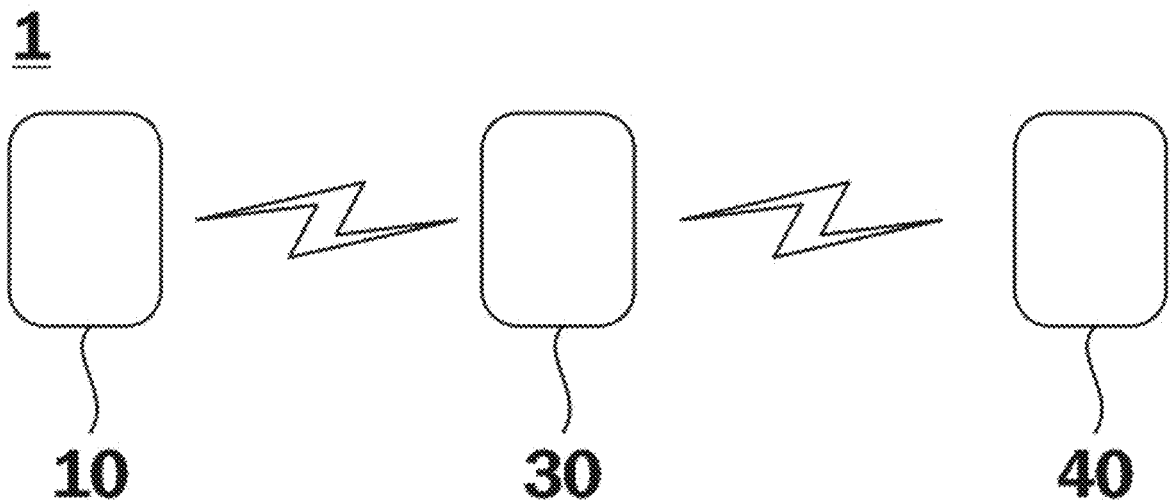
[Fig. 17]
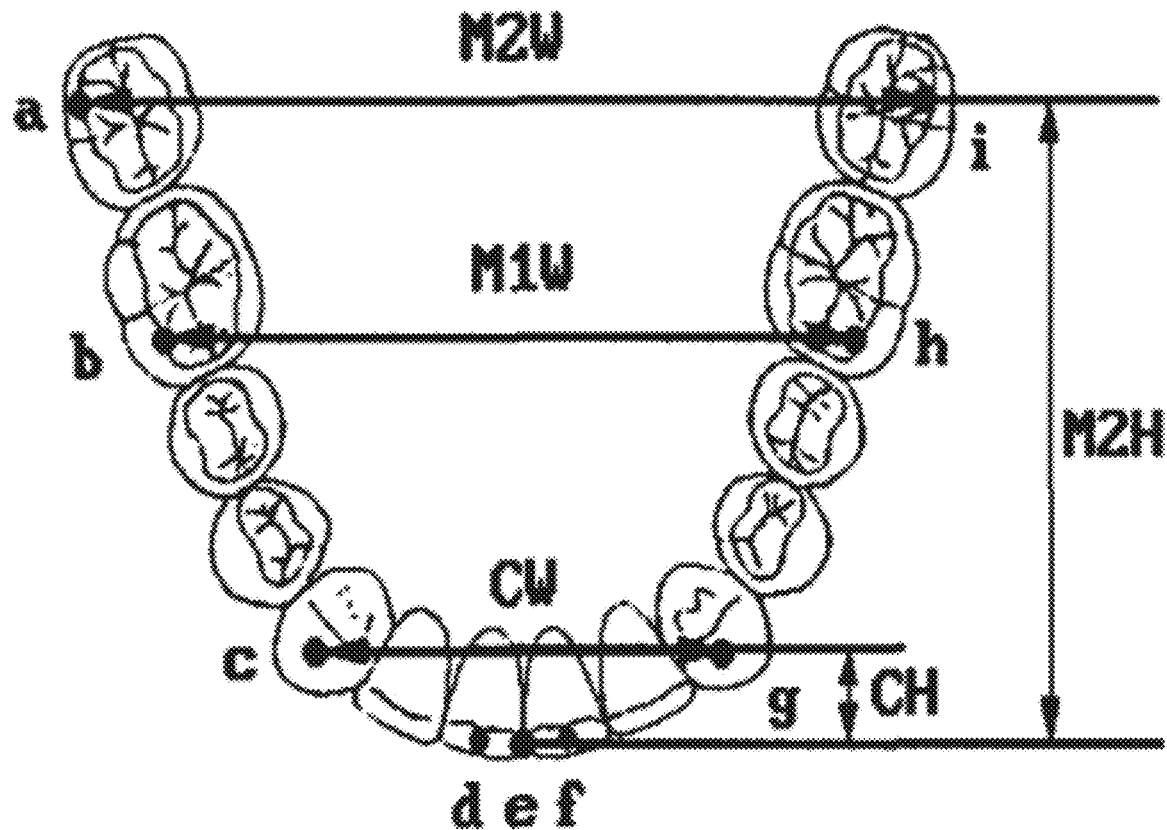

[Fig. 18]
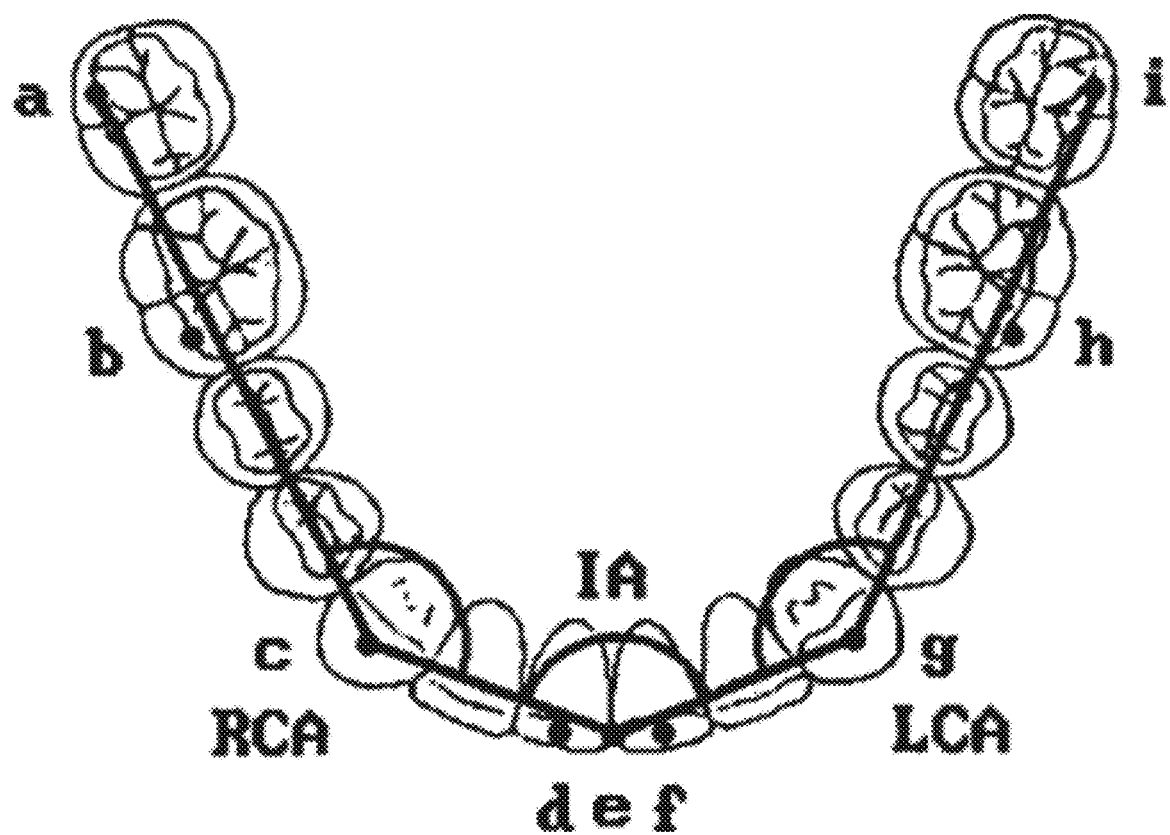

[Fig. 19]
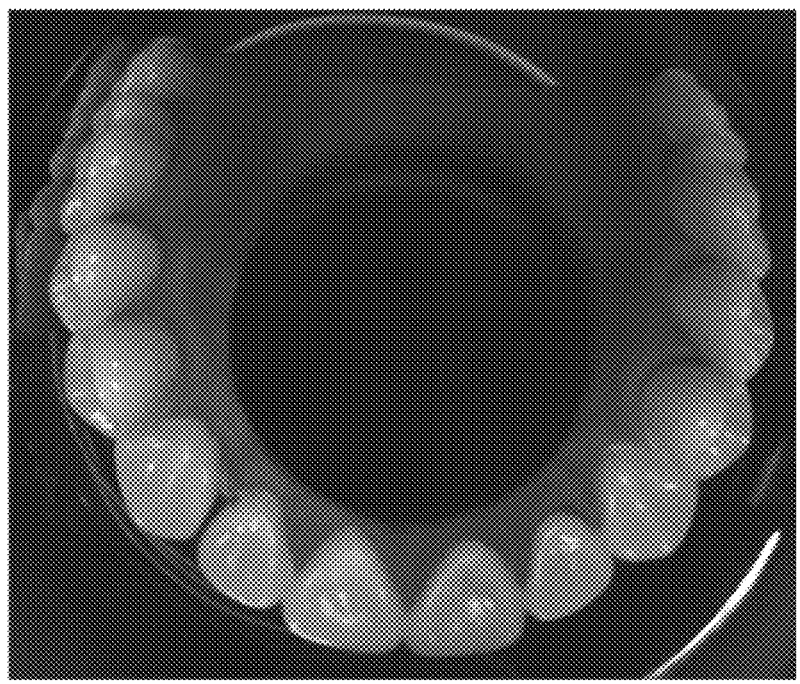
[Fig. 20]
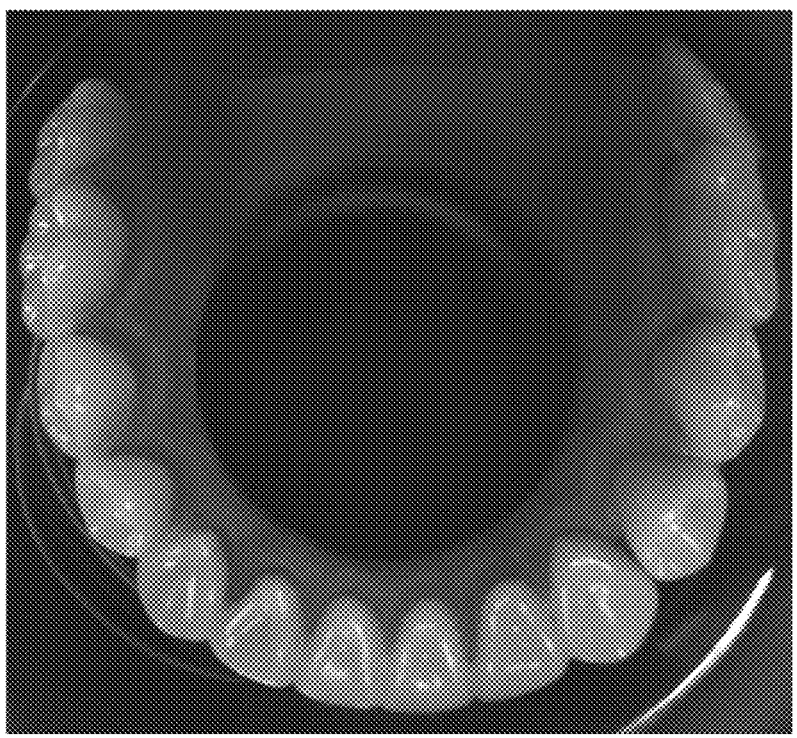

3D SCANNER AND ARTIFICIAL OBJECT PROCESSING DEVICE USING THE SAME

TECHNICAL FIELD

The present invention relates to an artificial object processing system including a three-dimensional (3D) scanner, a data converting device, a processing device/3D printing device, and the like, and more particularly, to a scanner capable of acquiring a 3D model of an oral cavity, a data converting device, and a processing device/3D printing device for processing an artificial object.

BACKGROUND ART

Non-contact type 3D scanners using a laser or light have a wide range of applications. That is, utilization of the non-contact type 3D scanners extends to almost every field in society, such as engineering, movie, animation, industrial design, medical care, artwork, fancy goods, duplicating materials and restoration of cultural properties, entertainment, etc.

In particular, in order to shorten manufacturing time of products in the industrial field, 3D scanners are used for the purpose of reducing cost in various stages from the development of produces to mass-production. Dealing with something that exists in reality as 3D digital data has many advantages. There is no work in a dangerous field each time, required information may be retrieved from a computer any time, and accurate 3D dimensions and shape information of real thing allows for a more accurate prediction of the future through simulating and replicating.

In addition, in the medical field, 3D scanners are used for manufacturing instruments customized to shapes of patients to manufacture orthodontic instruments, teeth, and the like. Traditionally, modeling methods using gypsum plaster are digitized using a 3D scanner. Orthodontic instruments, prosthetic appliance, prosthesis, dentures, etc., are designed through dedicated software on the basis of scanned 3D data and processed through CAM software. In particular, in dental field, an orthodontic treatment and restoration work are preceded by taking an impression, which is a concave shape of teeth of a patient to be treated and subsequently performing an operation of slip casting, which is a convex shape to become a die for a restoration operation. In addition, an overall process of modeling and producing customized artificial and implanted dentures for individual patients is performed manually according to a doctor's diagnosis. In particular, an operation of processing artificial and implanted dentures includes various complicated production process such as porcelain (traditional/old ceramics) fusing, mold-based casting molding, and the like. The overall processing process is totally dependent upon skill and psychological decision of a dental technician. In order to enhance precision and stability in the process of designing and producing artificial and implanted dentures, efforts to borrow a production process technique of an industrial field was already made by the NOBELBIO-CARE and CEREC teams in Switzerland 27 years ago. Even with such a technique, it is not easy to design a free-form surface of a tooth shape. In addition, due to limitations of production materials for processing such as CAM/CNC/RP, producing and forming artificial crowns suffered. In order to overcome the obstacle, technical challenges have continued by continuously developing techniques and making clinical tests steadily. Recently, as evolution of a digital technology and an artificial prosthesis material technology has accelerated, a combination of the dentistry and dental technology and CAD/CAM is transforming into an actual technology of fusion evolution beyond the technology of testing. Currently, various solutions and dental-only scanners are actively competing in the market.

Meanwhile, 3D scanners may be divided into a laser type scanner and a camera type scanner. The laser type scanner may scan objects in a point projection or beam projection measurement manner. The camera type scanner may scan objects in a projection or area measurement manner.

These 3D scanners have come to prominence in that they are able to measure an object at a high speed, precisely measure an elastic product, operate with a CAD having various purposes, and realize an accurate shape. However, the 3D scanners are disadvantageous in that they are significantly inferior to contact-type or 3D coordinate measuring process in terms of measurement precision, data post-processing is required in an overlapping shape of measurement areas, a significant error occurs when the entire image is obtained by combining a plurality of areas, and a process rate is delayed.

In order to measure an object using a 3D scanner, most generally, the object is imaged at various angles and matched points of respective scans are subsequently pointed by only a mouse by software to thus merge a plurality of scan images. This method, however, has a limitation in obtaining a precise 3D image due to a difference between combined images that occurs according to skill of users and requires not a little time for the merging operation.

Due to a lot of research and development to increase a 3D image processing rate of 3D scanners, the 3D image processing rate has recently been reduced to several minutes, but in a situation in which fast results are required to be obtained such as in a case where diagnosis results are required to be fed back to a patient in a medical practice, the current level of time required for obtaining a 3D image is evaluated not to come up to scratch.

DISCLOSURE

Technical Problem

An aspect of the present invention provides a 3D scanner capable of creating a 3D model by imaging a natural physiological oral structure (dental shape and angle, position and size of a tooth, etc.) of each patient without distortion as is, and an artificial object processing system using the same.

Another aspect of the present invention provides a 3D scanner capable of solving a 3D model alignment error and data processing time delay occurring when a subject is continuously imaged by regions in creating a 3D image and captured images are stitched to create a 3D model, and the like, as in the related art, and an artificial object processing system using the same.

Technical Solution

A 3D scanner of the present invention may include an imaging device including a first lens having a specific angle of view according to a refractive index, having at least one refractive surface and at least one reflective coating surface, and receiving an omni-directional image and a pattern generating device irradiating a light pattern to a subject, and the imaging device may receive an omni-directional image of the subject to which the optical pattern is irradiated. Also, the first lens of the 3D scanner according to an embodiment of the present invention may be configured as an aspherical lens which is any one of an omni-directional lens, a mirror-type lens, and a fish-eye lens.

In another aspect, the imaging device of the 3D scanner of the present invention may further include: a mirror unit changing a path of light from the first lens; and an image sensor obtaining an image from the mirror unit.

In another aspect, the 3D scanner of the present invention may obtain data for generating a 2D image and a 3D model of the subject. Here, the imaging device and the pattern generating device may be synchronized to thereby extract depth information of a 2D image and a 3D model may be generated therefrom.

In another aspect, the pattern generating device of the 3D scanner of the present invention may irradiate various light patterns in all directions using a second lens. The second lens may be configured as any one of an omni-directional lens, a mirror-type lens, and a fish-eye lens. In the 3D scanner of the present invention, the pattern generating device may include a light source, a light source modulator generating various patterns by adjusting the light source, and a micro-mirror irradiating various generated patterns. The light source may be configured as a single light emitting diode (LED) or a laser or as a plurality of the elements having various colors to generate a color pattern. The micro-mirror may be configured as a micro-electro-mechanical system (MEMS) mirror, a digital mirror device (DMD), or the like.

In another aspect, the pattern generating device may additionally include a cylindrical lens converting point light from the light source into line light, a special lens converting into a pattern of various grid shapes, and a collimator lens adjusting a size of a generated pattern to a size of the micro-mirror.

In another aspect, the 3D scanner of the present invention may include a display device displaying a 2D image obtained by imaging a subject, a 2D image divided by regions, or a generated 3D model data through wired and/or wireless communication, a portable display device, or a preview display device which may be configured in the 3D scanner. In the present invention, the subject may be an object having a shape such as a general structure, an object, animals and plants, a human body, an oral cavity, and the like, and in particular, refer to the teeth in an oral cavity and an oral cavity structure.

In another aspect, a data converting device of the present invention creates a 3D model from 2D image data and depth information received from the 3D scanner described above. The data converting device may design dentures, implants, braces, or surgical guides in the created 3D model and convert the same into computer aided manufacturing (CAM) data for a processing device or 3D printer.

In another aspect, a processing device of the present invention may process at least one of artificial tooth, bridge, implant, surgical guide, a brace, and a denture from the CAM data received from the data converting device described above. Also, the 3D printer may output at least one of artificial tooth and artificial gum, a plurality of teeth connected to palate, implant, surgical guide, a brace, and a denture from the CAM data received from the data converting device described above.

Advantageous Effects

In the embodiment, the 3D scanner may create a high-quality and highly precise 3D model by minimizing the occurrence of errors and degradation of precision and resolving power due to combination of images of the existing oral 3D scanner.

Further, in the embodiment, a 3D model may be created by rapidly photographing, even without applying powder for preventing light reflection to an oral cavity.

In addition, in the embodiment, time for imaging a tooth may be shortened, significantly shortening time for diagnosis such as a tooth, denture from a bridge, orthodontia, implant, and the like, a procedure plan and a procedure time.

In addition, in the embodiment, an operator is not required to perform a precise scan operation through minimization of the number of times of imaging a subject, a fast scanning rate, and a 3D model calibration operation based on rotation angle information, and thus, work efficiency of the worker may be enhanced, and a problem that precision of a 3D image is degraded due to variations between a plurality of captured images due to artificial vibrations such as hand-shaking or mechanical vibrations may be solved.

In addition, in the embodiment, satisfaction of a patient and a practitioner, which are subjects of the medical service, may be significantly increased by minimizing time for a treatment and diagnosis.

DESCRIPTION OF DRAWINGS

FIG. 1 is a view illustrating a three-dimensional (3D) scanner and a display device displaying an image received from the 3D scanner according to an embodiment of the present invention.

FIG. 2 is a cross-sectional view illustrating a first lens according to an embodiment of the present invention.

FIG. 3 and FIG. 4 are cross-sectional views of a first lens according to another embodiment of the present invention.

FIG. 5 is a configuration diagram of each device for explaining an image processing relationship between a 3D scanner and a data converting device.

FIG. 6 is a flowchart of image processing of a 3D scanner and a data converting device.

FIG. 7 is a view illustrating components of a pattern generating unit that may be applied to a 3D scanner of the present invention.

FIG. 8 and FIG. 9 are views for explaining a mode in which a line pattern reflected from a micro-mirror is irradiated to a subject.

FIG. 10 is a view for explaining a direction of a line pattern differentiated according to 90-degree rotation of a micro-mirror.

FIG. 11 is a diagram illustrating another example of a configuration of a pattern generating unit in FIG. 7.

FIG. 12 is a schematic view of a 3D scanner according to another embodiment of the present invention.

FIG. 13 is a schematic diagram illustrating a positional relationship between a first lens of an imaging device and a second lens of a pattern generating device.

FIG. 14 illustrates an example of generation of a line light pattern.

FIG. 15 is a schematic view of a 3D scanner having a projector unit according to another embodiment of the present invention.

FIG. 16 is a block diagram of an artificial object processing system using a 3D scanner according to an embodiment of the present invention.

FIG. 17 is a view of a mandibular arch.

FIG. 18 is a view illustrating an angle of a mandibular arch.

FIG. 19 is a view illustrating an image of a maxilla captured by a 3D scanner.

FIG. 20 is a view illustrating an image of a mandible captured by a 3D scanner.

BEST MODES

Hereinafter, a wireless power transfer system including a wireless power transfer system-charger according to an embodiment of the present specification will be described in detail with reference to the accompanying drawings. The following embodiments are provided as examples in order to convey the spirit of the present invention to those skilled in the art. Accordingly, the present invention is not limited to the following embodiments and may be variously embodied. In the drawings, the sizes and thicknesses of devices are exaggerated for convenience. The same reference numbers will be used throughout the drawings to refer to the same or like parts.

The advantages and features of the present invention and methods for achieving these will be clarified in detail through embodiments described hereinafter in conjunction with the accompanying drawings. However, embodiments of the present invention may, however, be implemented in many different forms and should not be construed as being limited to the embodiments set forth herein. Rather, these embodiments are provided so that this disclosure will be thorough and complete, and will fully convey the scope of the invention to those skilled in the art and are defined by the claim coverage of the present invention. Throughout the specification, the same reference numerals will be used to designate the same or like components. In the drawings, the sizes or shapes of elements may be exaggeratedly illustrated for clarity and convenience of description.

The terms used herein are for the purpose of describing particular embodiments only and are not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

<3D Scanner and Display Device>

FIG. 1 is a view illustrating a three-dimensional (3D) scanner and a display device displaying an image received from the 3D scanner according to an embodiment of the present invention.

Referring to FIG. 1, a 3D scanner 10 according to an embodiment of the present invention may include an omni-directional lens unit. The omni-directional lens unit may acquire a 360-degree omni-directional image. The omni-directional lens unit may include an omni-directional lens having a specific angle of view in a direction perpendicular to an omni-directional imaging plane depending on a refractive index. The omni-directional lens may be any one of a mirror-type lens, a fish-eye lens, and an aspherical lens. However, the omni-directional lens is not limited thereto and may be a lens configured to acquire image information regarding a structure of a tooth present in the lower jaw (mandible) S1 or an upper jaw (maxilla) S2 by acquiring a 360-degree omni-directional image, specifically, by performing imaging only one time.

The 3D scanner 10 may include a lens barrel part 11, a grip part 12, and a connecting part 13 connecting the lens barrel part 11 and the grip part 12. The connecting part 13 may be formed integrally or in combination with the barrel part to rotate the lens barrel part 11 on the grip part 12.

The entirety or a portion or an imaging device 610 (See FIG. 12) and a pattern generating device 620 (See FIG. 12) including the omni-directional lens may be embedded in the lens barrel part 11.

The grip unit 12 may be configured as an electronic device such as a wired or wireless communication module communicating with an external device, an image processing unit 320 processing an image signal from the imaging device, a driver controlling a micro-mirror, a light source and a light source modulator 512 generating a pattern, a memory storing image data before and after processing, a rotation angle information detecting unit, a lighting controller controlling illumination of the lens barrel part, and a controller controlling the components mentioned above.

A structure of the grip part 12 may have a shape such as a gun type with a handle, a handle type of a power grip type/grooming brush type, a pen type, and the like, and may have any shape as long as it allows a user to grip the grip part 12.

The connecting part 13 may be automatically rotated at a specific rotation angle by a lens barrel driving part 14 configured as an actuator such as a motor, or the like, or may be manually rotated. The lens barrel driving part 14 may be operated by external power or an internal battery.

When imaging a subject, at least a region of the lens barrel part 11 may approach the subject. When the subject is an oral cavity, at least one region of the lens barrel part 11 may be inserted into the oral cavity.

When a partial region of the lens barrel part 11 is inserted into the oral cavity, which is an example of the subject S, according to rotation of the lens barrel part 11 of the 3D scanner 10, all the regions of the oral cavity may be imaged. A 3D model may be created by simultaneously imaging the upper and lower jaws irrespective of a direction in which the light receiving region 15 is oriented. In detail, when the light receiving region 15 of the 3D scanner 10 inserted into the oral cavity faces one of the upper and lower jaws, any one of the upper and lower jaws may be imaged and at least one tooth, a set of teeth, the gum, and various oral cavity structures positioned in the upper and lower jaw regions of the oral cavity may be imaged to create a 3D model.

The integrated control device 20 of the present invention controls various functions between the 3D scanner 10 and the data converting device 30 and includes a power supply part of the 3D scanner and wired/wireless communication module handling communication between two parts. The wired/wireless communication module of the integrated control device 20 may include a commercialized existing device using a wireless communication scheme such as Wibro, Wi-Fi, and the like, a wired communication scheme such as a USB, serial, and the like, and a short-range communication scheme such as Bluetooth, RFID, and the like. Thus, the integrated control device 20 may handle a function of transmitting 2D image information captured by the 3D scanner and/or image information (depth information) in which a light pattern was irradiated to the subject, to the data converting device 30.

The data converting device 30 may correct an image distorted according to a curvature of the omni-directional lens (110a of FIG. 12) of the 3D scanner with a curvature value of the omni-directional lens and convert the image into a planar image. The planar image may be transmitted to the display device (31 of FIG. 5) and/or a preview display device 16 so that the image of the subject may be monitored.

As the display device of the data converting device of the present invention, a display device of a commercialized existing technology such as a liquid crystal display device (LCD), a field emission display device (FED), and an inputtable/outputtable touch screen may be used.

The 3D scanner 10 may extract 2D monitoring and depth information without distortion of the entire object, regardless of type of the subject. In the dental field, the 3D scanner 10 may provide depth information for generating a 2D image and a 3D image for detecting information such as a structure of a set of teeth including a defects such as cavities, plaques, and calculus in the entire upper or lower jaw, a shape and a size of a tooth, a position of a tooth. In addition, since the entire image of the set of teeth is obtained, rather than individually imaging the teeth, is obtained the individual tooth information may be extracted and displayed on the entire image.

In the related art method of generating a whole jaw by scanning each individual tooth and stitching the scanned individual teeth by the oral cavity 3D scanner, a significant error may occur in a merge/registration when the whole jaw is generated from the individual tooth. Thus, the related art is difficult to apply a finally produced prosthetic appliance to a patient.

Therefore, the 3D scanner of the present invention may overcome the problems and limitations of the related art and provide a high-precision/high-resolution 2D image and a 3D model.

<Omni-Directional Lens>

FIG. 2 is a cross-sectional view of a first lens for receiving an omni-directional image of the present invention, and FIGS. 3 and 4 are cross-sectional views of a first lens according to another embodiment of the present invention.

A first lens 110a may include a plurality of refracting surfaces and a plurality of reflection coating surfaces, but is not limited thereto.

The structure of the first lens 110a includes an outer refraction portion 111c for refracting an image of the subject at a desired angle of view, an inner refraction portion 116 having an inner reflective coating layer 117 for reflecting the subject image from the outer refraction portion 111c, a horizontal portion 113 having an outer reflective coating layer 114 for reflecting an image reflected from the inner refraction portion 116, and an inner concave portion 115 allowing the image of the subject reflected from the horizontal portion 113 to pass therethrough. Here, the outer refraction portion 111c may have a refraction angle and a distortion ratio to have a desired range of angle of view, and here, curvature of the outer refraction portion 111c may be smaller than curvature of the inner refraction portion 116 with respect to a virtual central axis CL of the first lens 110a. Also, the inner concave portion 115 may be formed at a central region of the inner refraction portion 116 to effectively transmit an omni-directional image to an image sensor.

The reflective coating layer 114 of the first lens 110a may be replaced with a reflection plate and a reflection plate may be disposed at the outer refraction portion 111c of the first lens 110a instead of the outer reflective coating layer 114.

Further, since the first lens 110a itself is formed as a spherical surface rather than an aspherical surface, it is possible to increase ease of processing and reduce manufacturing cost. In addition, the outer refraction portion 111c, the inner concave portion 115, and the inner refraction portion 116 are formed as spherical surfaces, making it possible to perform panoramic imaging, while solving the problem that it is difficult to process them the aspherical surfaces.

Meanwhile, for example, the angle of view may be from at least a portion of the outer surface of the lens, specifically, from a boundary between the region where the reflective coating layer 114 is formed and the region excluding the region, to an edge end.

Referring to FIGS. 3 and 4, the first lens 110a may include a first sub-lens 111x having a first incident surface 111d which is convex on one surface thereof, a first exit surface 111e formed on the other surface thereof, and a first reflective surface 111f formed at the center of the first incident surface 111d and a second sub-lens lily having a second incident surface 111g formed on one surface thereof, a second reflective surface 111h which is convex on the other surface thereof, and a second exit surface 111i formed at the center of the second reflective surface 111h, but the present invention is not limited thereto.

Joining surfaces of the first exit surface 111e and the second incident surface 111g may be formed to correspond to each other but not to be flat and may be in close contact with each other so as to be bonded.

An image of the subject incident through the first incident surface 111d may be reflected from the second reflective surface 111h after passing through the joining surfaces of the first exit surface 111e and the second incident surface 111g, and the image of the subject reflected from the reflective surface 111h may be reflected from the first reflective surface 111f after passing through the joining surfaces of the first exit surface 111e and the second incident surface 111g and subsequently exit through the second exit surface 111i after passing through the junction surfaces of the first exit surface 111e and the second incident surface 111g.

The first sub-lens 111x to which an external light source is incident and the second sub-lens 111y to be bonded to the first sub-lens 111x may be reflecting/refracting type lenses using reflection and refraction of a light source, and a 360-degree omni-directional image (i.e., panoramic image) may be obtained through the two lens.

The first reflective surface 111f and the second reflective surface 111h may be formed in various shapes such as a flat shape, a convex shape, or a concave shape, and may be coated with a material such as aluminum, silver, or the like, which may reflect a light source (image of the subject).

When a diameter of the second sub-lens lily is smaller than a diameter of the first sub-lens 111x and the first incident surface 111d is convex, the light source (image of the subject) incident from the outside may be refracted at a predetermined angle so as to be collected.

The structure of the exemplary first lens 110a has been described, but the present invention is not limited thereto.

Refraction angles and distortion rates of regions of each of the outer and inner surfaces of the first lens 110a may be determined in consideration of an average measurement value of human arches, measurement values of upper and lower arches and a tooth size, and combined biologic widths of child canine and premolar.

<3D Scanner and Data Converting Device>

FIG. 5 is a diagram illustrating a specific configuration of a 3D scanner and a data converting device according to an embodiment of the present invention, and FIG. 6 is a flowchart of image processing of a 3D scanner and a data converting device.

Referring to FIG. 5, the 3D scanner 10 may include an omni-directional lens unit 100 and an image sensor 18 capable of sensing an image of a subject from the omni-directional lens unit 100.

The omni-directional lens unit 100 may include an omni-directional lens capable of detecting a 360-degree omni-directional image and an image at a specific angle of view. The image sensor 18 may be required to have performance of high resolution to correct an image distorted due to a curvature of the omni-directional lens and may include RGB, RGB-IR, IR, time of flight (TOF), COMS, STACK, and so on.

The 3D scanner 10 may include a mirror unit 19 for converting an optical path and may be configured as a specially coated flat mirror, a prism, or the like. Here, the special coating refers to general coating for solving problems such as fogging, moisture, and foreign matter contamination, and the like.

In order to efficiently transfer an image from the omni-directional lens unit 100 to the image sensor 18, the 3D scanner 10 may include a lens array unit 200 having at least one lens between the two elements.

The 3D scanner 10 may further include an image processing unit 320, a communication unit (not shown), and a controller 310.

The image processing unit 320 may include elements such as an analog-to-digital converter (ADC), an amplifier, and an image processor for processing an image signal output from the image sensor 18, and here, an output from the image sensor may be an analog or digital signal. The image processing unit 320 may be configured in the data converting device 30 in FIG. 5 or may be independently configured, but is not limited thereto. The image processing unit 320 may transmit generated 2D image information and depth information to the data converting device 30 through the communication unit, and the data converting device 30 may create a 3D model of the subject using the 2D image information and the depth information.

The communication unit may be configured as a wired/wireless communication module for transmitting an image and information acquired by the 3D scanner 10 to the display device 31 and/or the data converting device 30. The display device 31 may be configured independently as in the embodiment of FIG. 5 or may be configured in the data converting device 30, but is not limited thereto.

The 3D scanner 10 may further include a rotation angle information detecting unit 330 which may be configured as a sensor capable of providing position information of a gyro sensor 331 or an acceleration sensor 332.

The rotation angle information detecting unit 330 may detect information such as a position, a tilt, and a rotation angle of the image acquired from the 3D scanner 10 on 3D reference coordinates to provide information for effectively creating a 3D model.

The controller 310 controls overall functions required for operating the 3D scanner 10. For example, the controller 310 may control driving of the image sensor 18, the image processing unit 320, a pattern generating device 17, a light source (not shown) illuminating the subject, a communication unit (not shown) capable of performing wired/wireless communication with the data converting device, or the like, and the rotation angle information detecting unit 330 and interworking therebetween.

The data converting device 30 of the present invention may be a computing device having any one of CAD, CAM, and CAD/CAM programs installed therein. Therefore, the data converting device 30 may create and design a 3D model of the subject on the basis of the image and depth information provided from the 3D scanner 10 and convert the 3D model into CAM data. The information refers to information such as a position, tilt, and a rotation angle of the rotation angle information detecting unit 330.

In detail, in the case of imaging the subject a plurality of times using the 3D scanner 10, if positions of the 3D scanner 10 differ at each image capturing time, pieces of coordinate information of a plurality of pieces of 2D image data do not match. Therefore, preferably, the pieces of coordinate information of the plurality of pieces of 2D image data match each other.

In an exemplary method for matching the pieces of coordinate information of the plurality pieces of 2D image data, software previously installed in the data converting device 30 may rotate, shift, and align positions of the pieces of 2D data may be rotated, shifted, and aligned on the basis of information from the rotation angle information detecting unit 330. Thus, since the data converting device 30 generates 3D data from the 2D image data using origin information and rotation angle information of the reference coordinate system, the positions are rapidly aligned and the amount of calculation is reduced, enhancing overall data processing rate. In addition, since the data converting device 30 may generate 3D data robust against fluctuations caused by factors such as hand trembling at the time of photographing by the user of the 3D scanner 10, quality of the image is significantly improved.

FIG. 6 is a flowchart illustrating a process of generating a 2D monitoring image and a 3D model. The flowchart includes imaging a subject with a 3D scanner; creating a 2D monitoring image from the captured image; detecting and correcting trembling of the captured 2D image; extracting depth information, position and rotation angle information from the captured image; generating position-aligned 3D data from the captured 2D image, depth, position, and rotation angle information; and creating a final 3D model of a subject from the position-aligned 3D data. However, creation of the 3D model is not limited to the order of the flowchart.

<3D Scanner having Pattern Generating Unit>

FIG. 7 is a diagram illustrating components of a pattern generating that may be applied to a 3D scanner of the present invention. FIGS. 8 and 9 are views illustrating a pattern in which line light reflected from a micro-mirror is formed on a subject. FIG. 10 is a view illustrating that a direction of line light is varied according to 90-degree rotation of a micro-mirror.

Referring to FIGS. 5 and 7 to 10, the 3D scanner 10 according to an embodiment of the present invention may further include a pattern generating unit 500.

The pattern generating unit 500 may include a light source modulator 510, a lens unit 520, and a micro-mirror unit 530.

The light generating unit 510 may include a light source modulator 512 or a driver and a light source 511. The light source 511 may be any one of various light sources such as a light emitting diode (LED) having a wavelength band such as visible light, infrared light, and the like, a laser diode, and the like. For example, the light source 511 may include a combination of red, green, and blue light source elements that may emit linear laser light, or alone. Thus, any light source may be applied to the 3D scanner 10 as long as it can generate and output light.

The light source modulator 512 may control driving of the light source 511 and a driving time using a binary signal, i.e., a pulse modulation signal, but the present invention is not limited thereto. For example, the light source modulator 512 turns on the light source 511 while the pulse modulation signal maintains a high level, and turns off the light source 511 while the pulse modulation signal maintains a low level.

The lens unit 520 may include a lens 521 in which radii of a vertical axis and a horizontal axis for outputting line light are different, like a cylindrical lens, a collimator lens 522, and the like. The cylindrical lens 521 has a semi-cylindrical shape, in which an incident surface for receiving light is non-curved surface and an exit surface for emitting received light may be a curved surface.

The collimator lens 522 may adjust a length of line light according to the size of the micro-mirror 531 and irradiate the line light having the adjusted length to the micro-mirror 531. That is, the collimator lens 522 may irradiate light received to be matched to the size of the micrometer 531 by focusing it to the micro-meter 531.

In another embodiment of the present invention, light from the light generating unit 510 may be directly irradiated to the micro-mirror 531, and a pattern may be irradiated to the subject.

In this case, in order to substantially reflect the light output from the micro-mirror 531, surface dimensions of the micro-meter 531 may be increased in proportion to an angle of an optical path from the light generating unit 510 and a distance between the light generating unit 510 and the micro-meter 531.

Further, the lens unit 520 is not limited to the above-described configuration but may be configured in various forms corresponding to exhibition of creation by an ordinary person skilled in the art.

The micro-mirror unit 530 reflects the line light output from the lens unit 520 to irradiate patterned light to the subject S and includes a micro-mirror 531 and a mirror controller 532 controlling driving of the micro-mirror 531. However, the present invention is not limited thereto, and the mirror controller 532 may be configured separately from the micro-mirror unit 530 or may be configured together with the controller 310.

The micro-mirror unit 530 may control up-down/left right rotational movement of the micro-mirror 531 by simultaneously or independently controlling a rotational shaft in a horizontal and/or vertical direction.

The micro-mirror 531 may be manufactured using micro-electro mechanical systems (MEMS) technology but is not limited thereto.

Light, which has passed through the collimator lens 522 on the optical path from the light generating unit 510 may be focused on a surface of the micro-mirror 531 so as to be reflected and may be converted into a line light pattern according to a rotation angle of the micro-mirror 531 so as to be irradiated to the subject S.

More specifically, the mirror controller 532 may determine a rotation angle about a longitudinal axis and/or transverse axis support of the micro-mirror 531. 2N lines/2M frame rates may be irradiated to the subject S when the micro-mirror 531 is rotated vertically and horizontally N or M times per second within the determined rotation angle range of the longitudinal axis and/or transverse axis support.

In the pattern generating unit 500 of the 3D scanner according to the present invention, a light source controlled by the light source modulator 512 outputs point light, and incident point light is converted into line light by the cylindrical lens 521 of the lens unit 520 so as to be output. Here, a thickness of the generated line light may be varied according to a high level duration of the pulse modulation signal of the light source modulator 512. The line light output from the cylindrical lens 521 is converted to a mirror size of the micro-mirror unit 530 by the collimator lens 522 of the lens unit 520. Therefore, the pattern generating unit 500 may irradiate various types of patterns to the subject by adjusting intervals between the line light and the line light having various thicknesses.

Although it is described that the lens unit 520 described above includes the cylindrical lens 521 and the collimator lens 522, the present invention is not limited thereto. That is, the lens unit 520 may include at least one lens configured to convert point light into line light and irradiate the converted line light to the micro-mirror unit 530.

The image sensor 18 may receive a pattern image sequentially irradiated onto the subject S.

In addition, a time at which the pattern image is irradiated to the subject and a time at which the pattern image is received by the image sensor 18 may be synchronized, and such synchronization may be performed by the controller 310.

In this case, the pattern generated by the pattern generating unit 500 and irradiated to the subject S may be distorted by unevenness of the surface of the subject S, but the data converting device 30 receiving the pattern image including distortion information of the pattern from the image sensor 18 may create an accurate 3D model of the subject S using the distortion information of the pattern.

The data converting device 30 or the 3D scanner 10 may include a memory, and as the sequential pattern is irradiated on the subject S, the image processing unit 320 may sequentially receive the pattern image and store the same in the memory. Also, the image processing unit 320 may extract data regarding 3D coordinates on the basis of image information stored in the memory, configure a wire frame using the extracted 3D coordinate data, and form a 3D model. However, the present invention is not limited thereto and the image information stored in the memory may be transmitted to an external device, and a 3D model of the subject S may be formed by the external device.

FIG. 11 is a diagram illustrating another configuration example of the pattern generating unit of FIG. 7.

Referring to FIG. 11, the lens unit 520 of the pattern generating unit 500 may receive light output from the light generating unit 510 and output light having various shapes such as a cross or radial shape using a structured illumination pattern lens 523.

The lens unit 520 may allow light having various structures to be output from the structured illumination pattern lens 523 and irradiated to the micro-mirror unit 530.

The lens unit 520 may be configured by the cylindrical lens 521 or the structured illumination pattern lens 523, may include the cylindrical lens 521 and an additional optical system, or may include the structured illumination pattern lens 523 and an additional optical system. In addition, a structure of light output from the lens unit 520 may vary depending on the degree of depth measurement, resolution, a focal point, and the like, according to types of the subject S.

Meanwhile, the data converting device 30 may use a triangulation technique algorithm to obtain 3D data of the subject in the data converting device 30 of the 3D scanner 10 of the present invention. The trigonometric algorithm may generate 3D data from an image of the subject irradiated with various patterns, distance information between the pattern generating unit 500 and the image sensor 18, and angle information therebetween. In other words, depth information for obtaining a 3D model of the subject may be obtained on the basis of a triangle formed by a specific point of the subject to which the pattern light is irradiated, the image sensor 18, and the pattern generating unit 500.

FIG. 12 schematically illustrates a 3D scanner according to another embodiment of the present invention. FIG. 13 schematically illustrates a positional relationship between a first lens of the imaging device and a second lens of the pattern generating device. FIG. 14 is a diagram illustrating an example of generation of a line light pattern.

Referring to FIG. 12, a 3D scanner 600 according to another embodiment may include an imaging device 610 located at reference numeral 11a and a pattern generating device 620 located at reference numeral 11b, and here, the imaging device and the pattern generating device are not limited to the above positions but may be disposed at any positions of the lens barrel part 11.

The imaging device 610 of the 3D scanner may include a first lens 110a having at least one refracting surface and reflective surface capable of receiving an image of 360 degrees in all directions with a specific angle of view according to a refractive index and the image sensor 18. Here, the first lens 110a may be an aspherical lens which is any one of an omni-directional lens, a mirror-type lens, and a fish-eye lens. Here, the angle of view may range from the edge of an outer surface of the lens to a boundary between a reflective coating surface and the other region. The imaging device 610 may include the image processing unit 320 and the controller 310. The controller 310 is illustrated to be included in the pattern generating device 620 but this is for the convenience of understanding and the controller 31 may control driving of both the imaging device 610 and the pattern generating device 620. Also, the imaging device 610 may further include a lens array unit 200 for effectively transferring light passing through the first lens 110a to the image sensor 18. The imaging device 610 may further include a mirror unit 19 for changing a path of light. These components have already been described above and a detailed description thereof will be omitted.

The 3D scanner 600 according to another embodiment of the present invention includes a pattern generating device 620. The pattern generating device 620 includes the light source 511 providing pattern light to the subject, the micro-mirror unit 530 including the micro-mirror 531 reflecting light from the light source 511, and a second lens 110b outputting light from the micro-mirror 531 in all directions. The micro-mirror unit 530 may control the micro-mirror 531 to tilt or rotate within a specific angle. Here, the micro-mirror 531 has a high frequency and thus it may operate very quickly. The second lens 110b may be an aspherical lens which is any one of an omni-directional lens, a mirror-type lens, and a fish-eye lens. The controller 310 may directly control the light source or control the micro-mirror 531 and synchronize a light pattern irradiation time of the pattern generating device 620 with a sensing time of the image sensor 18.

The micro-mirror 531 may be any one of a micro-electromechanical system (MEMS) scanning mirror, a uniaxial mirror, a biaxial MEMS scanning mirror, and a digital micro-mirror device (DMD).

Here, the DMD may be a device for projecting an image according to an ON/OFF state of reflection by a mirror element. The DMD, as a semiconductor optical switch integrated with a micro-driving mirror, may include a reflective mirror cell, which is an aluminum alloy micro-mirror having a size of tens to a few micrometers formed to correspond to each of memory cells of a static random access memory (SRAM), a cell driving unit, and a driving circuit unit. The DMD may additionally include elements such as a color wheel or a sequential color recapture (SCR) color wheel, and the like, to realize a color pattern.

The DMD type micro-mirror 531 has advantages that it has high color reproducibility according to a digital scheme, has a high contrast ratio so as to be bright and clear, does not require digital-to-analog conversion so as to be robust to noise, does not require or minimize correction of an additional signal, has high optical efficiency, has excellent durability as a perfect silicon device, and has a high operation rate.

A laser light line LL is irradiated in a laser light pattern form to the subject in the omni-directional region by the second lens 110b having a refractive index according to tilting or a rotation angle of the micro-mirror 531, and an image of the subject to which the pattern is irradiated is detected by the image sensor 18 of the imaging device 610. Also, the data converting device 30 may reconstruct a 3D model of the subject from the subject image information irradiated with various laser light patterns imaged from the image sensor 18.

A virtual straight line passing through a central axis of the first lens 110a may be perpendicular to the plane and a virtual straight line passing through a central axis of the second lens 110b may form a certain angle (theta) with a straight line perpendicular to the plane. Here, the theta angle (0 to 90°) may be determined on the basis of a structure and a shape of the 3D scanner 600, a predetermined distance d between the first lens 110a and the second lens 110b, a focal length, and the like.

The pattern generating device 620 may further include the lens unit 520. In order to efficiently transfer laser light, the lens unit may include a cylindrical lens 521, a collimator lens 522, and the like, and a lens for a special purpose may be added thereto. In addition, these components have already been described above and thus a detailed description thereof will be omitted.

The laser light is converted into a laser line LL by the lens unit 520, and the converted laser line LL is incident on/reflected by the micro-mirror 531 to form various types of laser light patterns.

FIG. 14 is an embodiment of the pattern generating devices 620 and 630 of the present invention.

The light source 511 may be a light source of at least one of red, green, and blue light emitting diodes and provide light of each of R, G, and B colors or various colors of light by combining the R, G, and B colors.

The laser light output from the laser light source is converted into line light by the lens unit 520, and the line light may be converted into line light patterns LLP having various thickness according to tilting or rotation of the micro-mirror 531 so as to be irradiated to the subject.

The lens unit 520 may include a structured illumination pattern lens, and in this case, the lens unit 520 may output may output light patterns having various structures.

FIG. 15 is a schematic view of a 3D scanner having a projector unit according to another embodiment of the present invention.

The pattern generating device 620 located at a region of reference numeral 11b of the 3D scanner 600 may be a projector unit 630 including a projector mirror 632, a projector 631, and a controller 310 for controlling the projector mirror 532 and the projector 631.

The projector unit 630 may include the second lens 110b and the projector mirror 632 may change a path of light irradiated from the projector 631.

The projector 631 may be a liquid crystal display (LCD) type projector, a liquid crystal on silicon (LCOS) type projector, or a digital light processing (DLP) type projector, but the present invention is not limited thereto and any device may be employed as the projector 631 as long as it can irradiate a pattern image to the subject.

The projector 631 may irradiate a pattern image including a gray pattern or a color pattern to the subject through the second lens 110b under the control of the controller 310. The image sensor 18 may detect the image of the subject irradiated with the pattern image using the first lens 110a. The data converting device 30 may convert a 2D image detected by the image sensor 18 may into a 3D model using the trigonometric algorithm.

The trigonometric algorithm used for generating a 3D model by the data converting device 30 is a method in which a unique identifier exists at each line formed by each pattern and a 3D model is created by generating 3D coordinates using an intersection point between a predetermined plane equation of a predetermined corresponding identifier and an actual position formed on the subject. Also, in order to obtain more accurate 3D coordinates, an inverse pattern may be used to obtain a pattern enhancement effect.

The 3D scanner 600 may have a memory in which various patterns may be stored. The controller 310 may control the pattern stored in the memory to be irradiated as pattern light of the projector 631 or may receive various patterns from an external device and store the same in the memory.

<Artificial Object Processing System>

FIG. 16 is a block diagram of an artificial object processing system 1 including the 3D scanner 10 capable of scanning an omni-directional image according to an embodiment of the present invention, the data converting device 30 capable of precisely creating a 3D model of a scanned subject, designing the created 3D model in various forms, and converting the designed 3D model into CAM data which can be processed by a processing device/3D printer 40, and the processing device/3D printer 40. A sub-device of the artificial object processing system 1 may transmit and receive data wiredly/wirelessly.

The data converting device 30 may create a 3D model from image data and depth information received from the 3D scanner 10. The data converting device 30 may design the created 3D model in various forms, converts the designed 3D model into CAM data, and provides the converted CAM data to the processing device/3D printer 40. Therefore, the data converting device 30 may be a CAD and/or CAM-based data converting device capable of capturing and processing a 2D image of the subject, but the present invention is not limited thereto and any device may be employed as the data converting device as long as it can create a 3D model of the subject using image data captured from the 3D scanner and converting the created 3D model into CAM data.

The processing device/3D printer 40 may create an artificial object used for dental treatment, diagnosis, treatment, and prevention such as prosthetic appliance, implants, braces, or surgical guides using the received CAM data.

FIG. 17 is a view of a mandibular arch and FIG. 18 is a view illustrating an angle of the mandibular arch.

The image processing unit 320 or the data converting device 30 of the 3D scanner 10 of the present invention may provide various types of precise information on an oral cavity such as shapes and sizes of dental arches of the upper and lower jaws, angles of the dental arches, shapes and sizes of individual tooth, distances between teeth, and the like, on the basis of the created 3D model, and display the corresponding information on the display device 31 of the preview display device 16.

<Captured Image of Maxilla/Mandible>

FIG. 19 shows an example of an image of maxilla (upper jaw) that may be captured by a 3D scanner of the present invention, and FIG. 20 shows an example of mandible (lower jaw).

FIGS. 19 and 20 are images captured by an omni-directional lens and may be displayed as 2D images or panoramic images processed by the data converting device 30 or the image processing unit 320 so as to be divided by certain regions, in which the black regions in the middle of the images may correspond to palate, tongue, and the like, which may be image-processed or removed.

Conventional oral 3D scanners have a limited field of view (FOV), Therefore, the conventional oral 3D scanners cannot image the entire maxilla or mandible at one time and capture a plurality of images as many as measurement areas to image the entire maxilla or mandible. In contrast, the 3D scanner of the present invention may capture an image of the entire region of a subject by the omni-directional lens at one time. Accordingly, the 3D scanner of the present invention minimizes the occurrence of errors and the degradation of precision and resolution due to the combination of the images of the conventional oral 3D scanner, thus creating a high-quality and high-precision 3D model. In addition, the 3D scanner of the present invention may create a 3D model by rapidly performing imaging even without applying powder for preventing light reflection to the oral cavity. Therefore, it is possible to shorten time for imaging a tooth, which may significantly reduce diagnosis, a procedure plan, and procedure time of teeth, bridge, denture, tooth correction, and implant.

The 3D scanner of the present invention may be applied to fields other than the dental field. For example, the 3D scanner of the present invention may be applied to an equipment inspection field for inspecting semiconductor equipment, PCB mass-production, and the like, a medical field such as plastic surgery or prosthetic leg/prosthetic hand, facial recognition, 3D model by an endoscope, an industrial field such as precisely scanning a structure of a certain space which is difficult to check with naked eyes or restoration of cultural properties, and the like.

The 3D scanner of the present invention may adopt various scanning schemes capable of creating a 3D model such as a stereo/video scheme, a still image scheme, and the like, and this may be realized by any one of the schemes mentioned above in the data converting device.

As described above, in the 3D scanner and the artificial object processing system using the 3D scanner of the present invention, since the lens is configured to output an light pattern at 360 degrees in all directions and/or capture an image at 360 degrees in all directions, a 3D model may be realized by imaging the entire region of the subject at one time. Thus, it is possible to solve an error problem due to combination of the partial images of the subject and a cumulative error problem due to an increase in the number of the partial images and to minimize time required for creating the 3D model of the entire subject.

Also, in the 3D scanner and the artificial object processing system using the 3D scanner according to the present invention, since the aspherical lens for obtaining an omni-directional image and the pattern generating device for irradiating pattern light to the subject are provided, a possibility of the presence of a surface region of the subject not measured by the image processing unit may be eliminated. Thus, the angle of the triangulation technique may be increased as much as possible in generating a 3D image according to the triangulation technique, whereby accuracy and quality of the 3D image and resolution of the 3D image may be significantly improved.

According to the present invention, since the operator is not required to perform a precise scanning operation through minimization of the number of times of imaging the subject and a 3D model calibration operation based on a fast scanning rate and rotation angle information, operation efficiency of the operator may be enhanced, and a problem that precision of the 3D image is degraded due to variations between a plurality of captured images due to artificial vibrations such as handshaking or mechanical vibrations may be solved.

In case where the embodiment of the present invention is used for a medical purpose, satisfaction of a patient and a practitioner, which are subjects of the medical service, may be significantly increased by minimizing time for a treatment and diagnosis.

The present invention has been described with reference to the embodiments but it is to be understood that the present invention may be variously changed and modified without departing from the spirit and scope of the invention described in the claims by a person skilled in the art or a person of ordinary skill in the art. Therefore, the technical scope of the present invention should not be limited to the contents described in the detailed description of the specification but should be defined by the claims.

INDUSTRIAL APPLICABILITY

The present invention may be used in the field of scanning a subject three-dimensionally and processing an artificial object regarding the subject using the same.

The invention claimed is:

1. A 3D scanner comprising:
a pattern generator irradiating a light pattern to a subject; and
an image receiver receiving an omni-directional image of the subject to which the light pattern is irradiated,
wherein the image receiver includes a first lens, the first lens having a specific angle of view according to a refractive index, the first lens having at least one refractive surface and at least one reflective coating surface.

2. The 3D scanner of claim 1, wherein
the image receiver further includes:
a mirror unit changing a path of light from the first lens; and
an image sensor sensing light from the mirror unit.

3. The 3D scanner of claim 2, wherein
data for generating a 2D image of the subject or a 3D model of the subject is generated on the basis of reading of the image sensor.

4. The 3D scanner of claim 2, wherein
the image receiver synchronizes a time at which the pattern generator irradiates the light pattern and a time at which the image sensor senses light.

5. The 3D scanner of claim 1, wherein
the first lens is aspherical lens which is any one of an omni-directional lens, a mirror-type lens, and a fish-eye lens.

6. The 3D scanner of claim 1, wherein
the pattern generator irradiates the light pattern to the subject in all directions.

7. The 3D scanner of claim 1, wherein
the pattern generator includes a second lens irradiating the light pattern in all directions.

8. The 3D scanner of claim 7, wherein
the second lens is any one of an omni-directional lens, a mirror-type lens, and a fish-eye lens.

9. The 3D scanner of claim 7, further comprising:
a rotation angle information detecting unit detecting rotation angle information of the 3D scanner for generating or correcting a 3D model of the subject.

10. The 3D scanner of claim 9, wherein
the rotation angle information detecting unit includes a gyro sensor and an acceleration sensor.

11. The 3D scanner of claim 9, wherein
the pattern generator further includes:
a micro-mirror forming the light pattern on the subject; and
a light source irradiating light to the micro-mirror.

12. The 3D scanner of claim 11, wherein
the light source includes at least one light emitting diode (LED) or laser.

13. The 3D scanner of claim 11, wherein
the pattern generator further includes:
a lens, in which a radius of a longitudinal axis and a radius of a transverse axis are different, converting light from the light source into line light and irradiating the converted line light to the micro-mirror; or
a structured illumination pattern lens converting light from the light source into a light pattern having a predetermined structure and irradiating the converted light pattern to the micro-mirror; and
a collimator lens focusing and irradiating the line light or the light pattern having the structure to the micro-mirror.

14. The 3D scanner of claim 11, wherein
the pattern generator includes a light source modulator controlling at least one of a driving time and a driving period of the light source, adjusting intervals between light lines and thicknesses of the light lines irradiated to the subject, and generating a plurality of colorful or unicolor patterns in various forms.

15. The 3D scanner of claim 11, wherein
the subject is an oral cavity.

16. The 3D scanner of claim 1, wherein
a 2D image obtained by imaging the subject, an image obtained by dividing the 2D image into certain regions, or a 3D model of the subject is transmitted to at least one of a display, a portable display, and a preview display installed in the 3D scanner through wired and/or wireless communication.

17. The 3D scanner of claim 1, comprising: a data converter converting image data received from the 3D scanner into a 3D model to generate design data, and converting the generated design data into data including CAM data which can be processed by a processor or a 3D printer.

18. The 3D scanner of claim 17, comprising: a processor generating at least one of a gum of at least one artificial tooth and an artificial object, a plurality of teeth connected to palate, implant, surgical guide, a brace, and a denture on the basis of the CAM data received from the data converter.

19. The 3D scanner of claim 17, comprising: a 3D printer generating at least one of a gum of at least one artificial tooth and an artificial object, a plurality of teeth connected to palate, implant, surgical guide, a brace, and a denture on the basis of the CAM data received from the data converter.

* * * * *